United States Patent
Sahiri et al.

(10) Patent No.: US 9,297,760 B2
(45) Date of Patent: Mar. 29, 2016

(54) APPARATUS FOR ANALYSING A SMALL AMOUNT OF LIQUID

(75) Inventors: Thomas Sahiri, Calabasas, CA (US); Stefanie Greiffenreich, Neuenburg (DE); Holm Kandler, Auggen (DE); Christof Koltunski, Merzhausen (DE)

(73) Assignees: Hellma Gmbh & Co., KG, Mullheim (DE); Thomas Sahiri, Calabasas, CA (US)

( * ) Notice: Subject to any disclaimer, the term of this patent is extended or adjusted under 35 U.S.C. 154(b) by 40 days.

(21) Appl. No.: 14/004,409

(22) PCT Filed: Mar. 12, 2012

(86) PCT No.: PCT/EP2012/054238
§ 371 (c)(1),
(2), (4) Date: Jan. 27, 2014

(87) PCT Pub. No.: WO2012/123395
PCT Pub. Date: Sep. 20, 2012

(65) Prior Publication Data
US 2014/0158911 A1    Jun. 12, 2014

(30) Foreign Application Priority Data
Mar. 11, 2011   (DE) .......................... 10 2011 005 432

(51) Int. Cl.
*G01N 1/10* (2006.01)
*G01N 21/64* (2006.01)
(Continued)

(52) U.S. Cl.
CPC ............ *G01N 21/64* (2013.01); *G01N 21/0303* (2013.01); *G01N 21/59* (2013.01); *G01N 21/645* (2013.01); *G01N 21/65* (2013.01); *G01N 2021/035* (2013.01)

(58) Field of Classification Search
CPC .............. G01N 2021/0346; G01N 2021/0392; G01N 21/03; G01N 21/05; G01N 21/59
USPC .................... 356/244, 246, 432–440, 301; 250/227.11, 458.1
See application file for complete search history.

(56) References Cited

U.S. PATENT DOCUMENTS 6,490,034 B1   12/2002 Woias
6,747,281 B2    6/2004 Sendai et al.
(Continued)

FOREIGN PATENT DOCUMENTS

DE        3718407      12/1988
DE   102004034977 A1   2/2006
(Continued)

OTHER PUBLICATIONS

International Search Report; App. No. PCT/EP2012/054238; May 9, 2012; pp. 1-2.
(Continued)

*Primary Examiner* — Hoa Pham
(74) *Attorney, Agent, or Firm* — Knobbe Martens Olson & Bear LLP

(57) ABSTRACT

An apparatus (1) for analyzing, measuring the fluorescence, luminescence, phosphorescence, Raman scattering or absorption of a small amount, for example a drop, of a liquid sample (2) with the aid of light (3) which can be guided through the sample (2) and can then be detected or analyzed according to said measuring methods. Said apparatus comprises a sample holder which is at the top when in the position of use and has a receiving point (4) for applying or dripping the sample (2), and a light inlet (5) for excitation light, said light inlet being horizontally oriented when in the position of use and below the sample holder (4). The apparatus has a first device (7) which is downstream of the light inlet (5) in the beam path and is used to deflect the light upwards to a position to the side of the receiving point (4), and second light deflection means (8) which guide the light beam coming from the bottom into the sample to be analyzed.

15 Claims, 6 Drawing Sheets

(51) Int. Cl.
*G01N 21/03* (2006.01)
*G01N 21/65* (2006.01)
*G01N 21/59* (2006.01)

(56) References Cited

U.S. PATENT DOCUMENTS

| | | | |
|---|---|---|---|
| 6,809,810 B2 * | 10/2004 | Carrillo | 356/246 |
| 6,891,620 B2 * | 5/2005 | Mukai et al. | 356/445 |
| 7,202,945 B2 | 4/2007 | Erlbacher et al. | |
| 7,397,036 B2 | 7/2008 | Robertson et al. | |
| 7,483,138 B2 | 1/2009 | Sahiri et al. | |
| 7,952,705 B2 * | 5/2011 | Shen et al. | 356/246 |
| 8,570,508 B2 * | 10/2013 | Rose et al. | 356/326 |
| 2002/0185608 A1 | 12/2002 | Wieser | |
| 2006/0012785 A1 | 1/2006 | Funk et al. | |
| 2006/0135861 A1 | 6/2006 | Lucassen et al. | |
| 2007/0229946 A1 | 10/2007 | Okada et al. | |
| 2009/0156429 A1 | 6/2009 | Scott et al. | |
| 2009/0290150 A1 | 11/2009 | Takimoto et al. | |
| 2010/0201784 A1 | 8/2010 | Lippert et al. | |
| 2010/0265318 A1 | 10/2010 | Bewersdorf et al. | |
| 2010/0283835 A1 | 11/2010 | Bewersdorf et al. | |

FOREIGN PATENT DOCUMENTS

| | | |
|---|---|---|
| DE | 102004023178 B4 | 6/2006 |
| DE | 60123884 | 5/2007 |
| DE | 102005036898 B4 | 1/2008 |
| DE | 102007045897 | 4/2009 |
| EP | 0660106 B1 | 4/1998 |
| WO | WO 94/27137 | 11/1994 |
| WO | WO 97/35181 | 9/1997 |

OTHER PUBLICATIONS

Huisken et al., N.N.: SPIM—ein neues Mikroskopieverfahren. in: Innovation, Carl Zeiss AG, 2005, vol. 15, S. 34-37 (including English language translation).

* cited by examiner

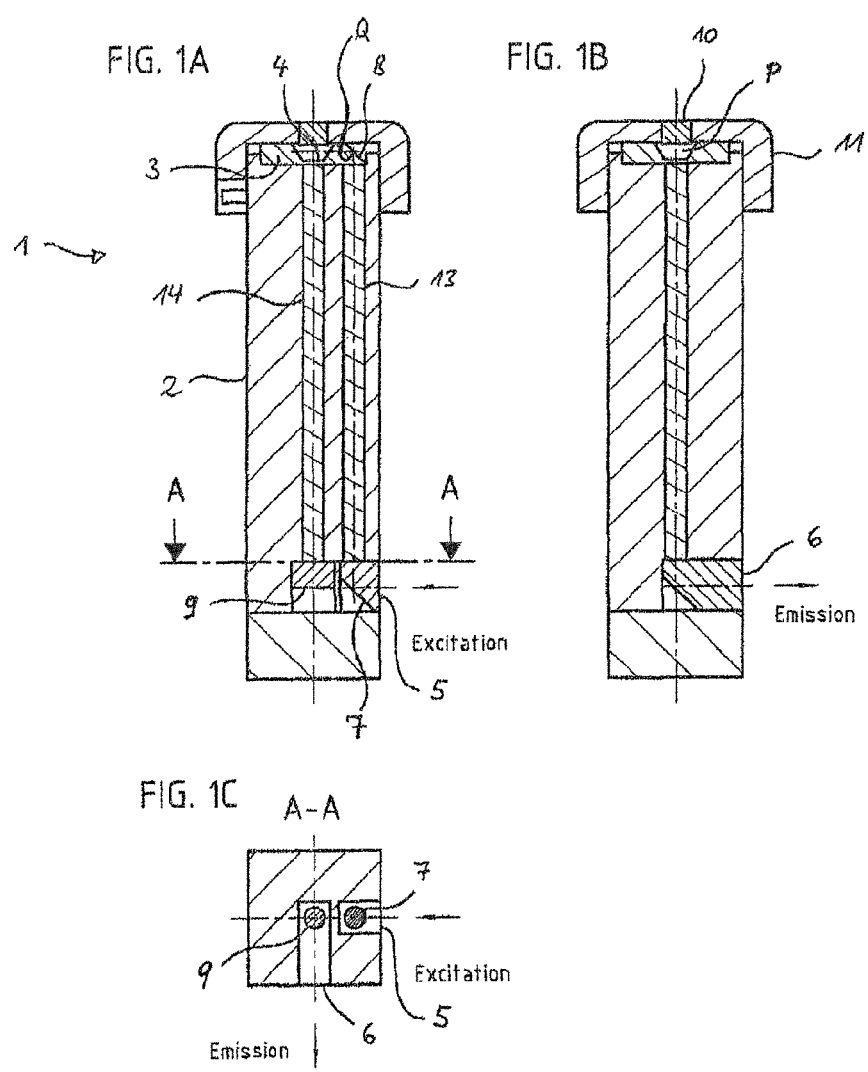

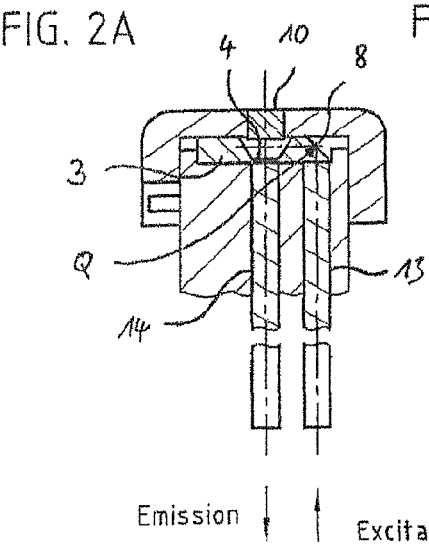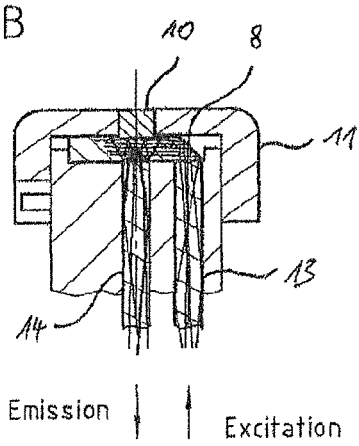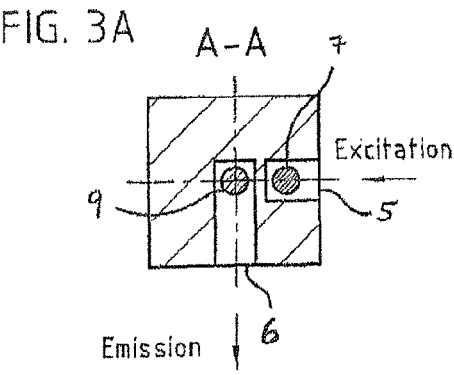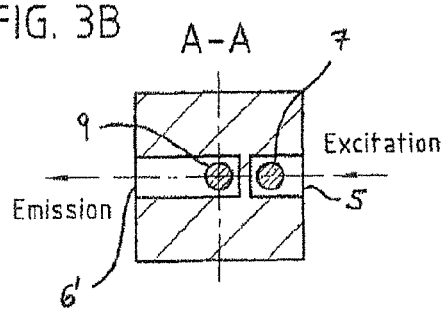

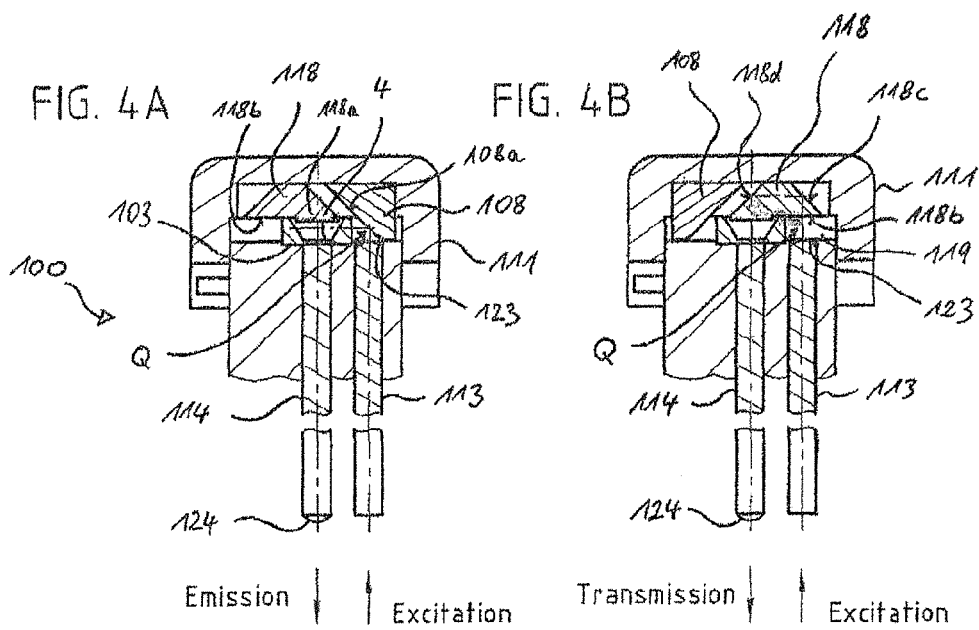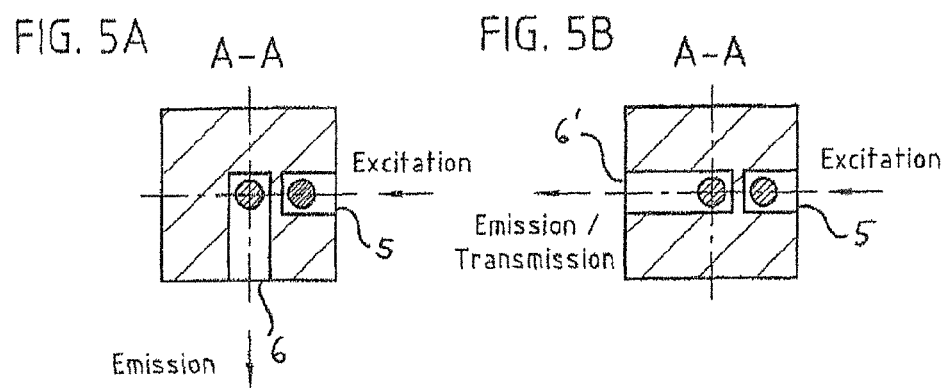

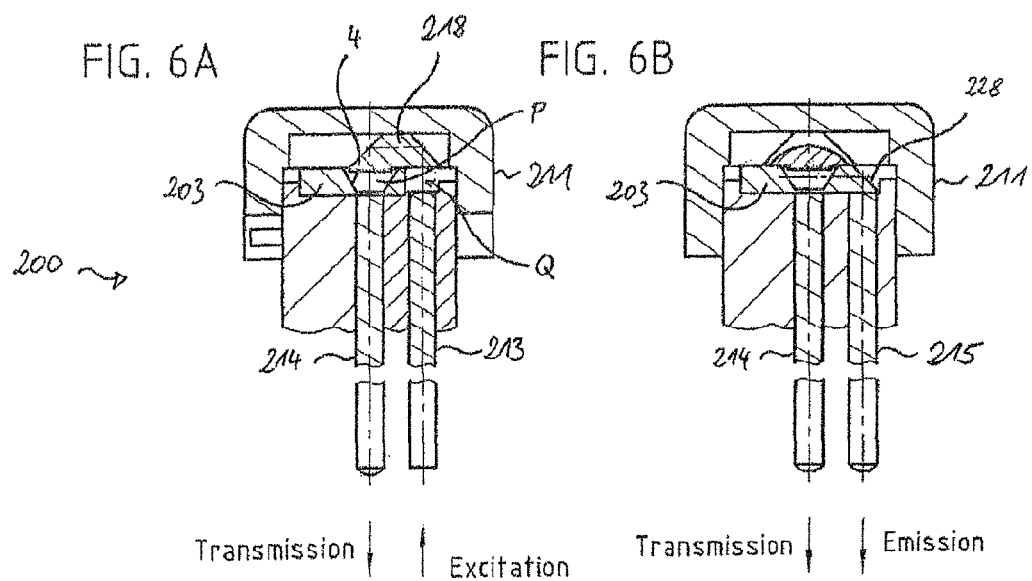
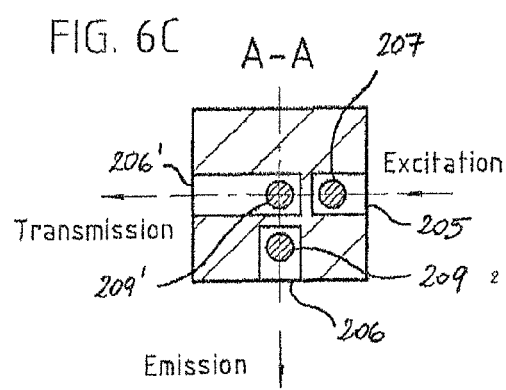

APPARATUS FOR ANALYSING A SMALL AMOUNT OF LIQUID

INTRODUCTION

The invention concerns an apparatus for analysing, measuring the fluorescence, luminescence, phosphorescence, Raman scattering or absorption of a small amount, for example a drop, of a liquid sample using light which is guided through the sample and can then be detected or analysed according to said measurement methods, wherein the apparatus has an upper receiving point which is flat in the working position, for application or dripping of the sample, a light inlet which is oriented horizontally in the working position in its housing below the receiving point, and a first device arranged downstream of the light inlet in the beam path to deflect the light upwards to the receiving point, and a second light deflector which deflects the light beam coming from below into the sample to be analysed.

PRIOR ART

A similar apparatus is described in German patent DE 10 2004 023 178 B4 and has proved useful in practice as a universal accessory for absorption measurement. It has however been found in particular that on fluorescence measurements, due to the direct deflection of the excitation light in the direction of the detector by means of the detachably mountable reflector, the detector is over-irradiated with too great a quantity of light. As a result the detector can become saturated and sometimes damaged. At least the exciting radiation cannot be distinguished from the fluorescent radiation, which is substantially weaker in intensity, and analysis of the measurement signal is not therefore possible.

The similar solution known from German patent DE 10 2005 036 898 B4 has also been tried since the availability of a smaller construction height was found to be a critical success factor for the universal applicability as an accessory. However in fluorescence measurements, the same undesirable effects occur as explained above.

EP 0 660 106 A1 discloses an apparatus which allows performing measurements at greater distances with a conventional spectrophotometer having a receiver shaft for insertion of a measurement cell. The apparatus also has the exterior dimensions of such a cell and thus fits in the receiver shaft of the spectrophotometer. Light deflectors in the form of prisms or mirrors are provided in the apparatus, whereby firstly the incident light is deflected to a first light guide which guides it to a remote measurement point on a probe. A second light guide returns the light and deflects it into the apparatus through a second deflector in the form of a prism or a mirror to the point at which the light guided through the measurement cell emerges to a detector.

In commercial fluorimeters and spectral fluorimeters and the fluorescence cells used for receiving and holding the liquid samples to be examined, an angle of 90° has been established for the decoupling of exciting radiation and emitted radiation from a fluorescing sample, wherein in principle any other angle would be suitable which mutually decouples the numerical apertures of the exciting radiation and the emitted radiation. The disadvantage here is the sample quantities which must be used, from at least around 20 µL up to one or more milliliters.

U.S. Pat. No. 7,397,036 B2 describes a variant of the 90° arrangement of the exciting radiation and received emitted radiation which allows a fluorimetric analysis of small sample amounts of around 2 µL, wherein the sample to be analysed is held as a liquid column solely by the surface tension in a special sample receiver apparatus between two plungers. The sample volume examined depends on the pipetting accuracy or the sample quantity which remains in the liquid column and is caused by the respective surface tension. Measurement of conventional samples on organic basis is therefore largely excluded. The open arrangement of the sample receiver device means that the necessary protection from false light is not sufficiently guaranteed.

OUTLINE OF THE INVENTION

Therefore, the object exists of creating a universally applicable apparatus of the type described initially in which the advantages of placing in a simple manner small sample amounts of precisely defined volume of a liquid sample, even with low surface tension, at a measurement point, and after measurement being able to perform a reliable and simple cleaning, are achieved equally with large and small construction heights, but now a fluorescence measurement is possible with sufficient differentiation of the exciting radiation and emitted radiation.

This object is achieved with an apparatus for analyzing, measuring the fluorescence, luminescence, phosphorescence, Raman scattering or absorption of a small amount of a liquid sample. Advantageous refinements of the invention are described below.

To achieve this object, in the apparatus defined initially a first device (light deflector) is provided which is located downstream of the light inlet in the beam path, for deflection of the light upwards at a position to the side of the receiving point, and a second light deflector which deflects the light beam coming from below into the sample to be analysed (towards the receiving point). The second deflector can be arranged at the side in the region of the sample holder and thus deflect the light into the liquid sample at a suitable angle so that no part of the exciting radiation is deflected in the direction of the detector, the emission beam path and excitation beam path are therefore separated from each other. Here, in contrast to the apparatus defined initially, not only is the side of the sample receiving point facing the deflector made light-permeable but also its side boundaries, wherein the term "light-permeable" relates to the excitation and signal radiation used.

To minimise losses on transport within the apparatus, it is advantageous to integrate the second light deflector in the side boundaries of the sample holder so that this is able to deflect the excitation light, for fluorescence excitation, horizontally into the sample (towards the receiving point). Accordingly on horizontal excitation, the fluorescence is emitted at 90° in the vertical direction upward and downward and, because of the second light deflector arranged next to the sample receiving point, is therefore perpendicular to the exciting radiation in the sample and hence spatially separated therefrom.

If the beams run substantially vertically due to the design of the first light-deflecting element and the subsequent beam guidance to the receiving point, and due to a corresponding beam guidance from the receiving point back in the direction of the detector, the construction height of the apparatus can be varied arbitrarily within a wide range since, because of the second light deflector, there is no influence on the function at the actual measurement point, namely the sample receiving point recessed in the manner of a dish.

The sample receiving point is preferably a recess in the sample holder. This recess can be indented flatly and horizontally, and is delimited peripherally at the side. Thus dish-like recesses with chamfered side walls, and cylindrical recesses with vertical side walls, or other shapes of sample receiving point can be considered as long as these allow a precise definition of the sample volume in the receiving point.

Since depending on application, it can be important to know the precise volume of the sample analysed also in fluorescence measurements, the receiving point is preferably closed or delimited at the top. This delimitation can be provided by a lid and is preferably flush. It is also possible for the receiving point to be delimited by a reflector with horizontal reflection surface for the fluorescence radiation, preferably also flush. The reflector can also be integrated in the lid and thus delimit the receiving point in said manner. Here the sample receiving point which is precisely defined by its size or volume is of particular advantage, since it gives a measurement chamber which is geometrically defined in all spatial directions. It is guaranteed that firstly organic media which have only a low surface tension remain in the measurement chamber, and at the same time the volume is clearly defined. As a result there is no dependency on pipetting accuracy since the volume examined depends purely on the geometry of the measurement chamber.

The boundary of the sample receiving point, as in a fluorescence cell, can also be designed angularly, wherein for ease of cleaning it is preferred if the boundary is designed cylindrical or in the form of a downwardly tapering truncated cone. This shape is not relevant for the optical function.

The reflector can also be replaced by another element delimiting the measurement chamber, but it can enlarge the spatial angle of the fluorescence light detected for measurement and thus amplify the signal. As an alternative to a flat reflector, a transparent element delimiting the measurement chamber is conceivable which on its back has a curved or spherical reflecting surface which reflects the emitted fluorescent light in the direction of the detector.

Since the reflector is preferably housed in a lid-like element, the sample receiving point is protected from false light. False light can prevent the determination of precise measurement results, in particular on weak fluorescence signals.

All construction elements delimiting the measurement chamber are advantageously designed such that the materials used are free from fluorescence and their edges and surfaces do not by their composition generate any scattering which can be directed towards the detector.

The first light deflector can take the form of a total internal reflection prism or another reflective component, for example a metal-coated mirror.

The light conduction from the first deflector to the receiving point can also advantageously take place with light conductor rods, light guide fibres of large cross section, or fibre bundles. With a well-collimated exciting radiation, such as would be the case for example with a laser radiation source, in principle light-conductive components can be omitted and the exciting radiation transported directly from the first deflector to the second deflector.

The light conduction from the base of the receiving point to the first detector light deflector, which deflects the light towards the detector, functions in a similar manner. Because of the need to deflect a sufficiently strong light signal from the actual measurement point in the direction of the detector, light guidance by means of light-conductive components in this section is in practice unavoidable.

The first detector light deflector can again be a total internal reflection prism or another reflective component. It is also conceivable to integrate the prism for example in the end of said light conductor rod, in that its end is provided with a reflective surface arranged at an angle.

As already stated, in the present apparatus the actual measurement point is located in the region of the upper receiving point in the angular arrangement of excitation beam and emission beam favourable for fluorescence measurement. Thus an essential aspect of the invention described is the independence from the device-side arrangement of the exciting radiation, and the necessary orientation of the emitted radiation towards the detector.

Firstly it is preferably possible to select fluorescence meters as an application for the apparatus. Here in commercial equipment, the arrangement of exciting radiation and the necessary orientation of the emitted radiation in the direction of the detector typically takes place at an angle of 90°, with other angles being conceivable.

Similarly it is now however possible to use for fluorescence measurement some photometers or spectrophotometers which are actually intended for absorption measurements or transmission measurements. Equipment which on the detector side has a polychromator, so-called diode-array devices, or equipment which can select the wave length range to be analysed via the spectral filter, are particularly evident and universally applicable. In relation to exciting radiation, the excitation wavelength can also be determined at the outlet from the lamp module by the use of simple spectral filters which are available at low cost as catalogue goods, for example from Edmund Optics.

As well as the possibility of measuring fluorescence, in a constructional variant according to a second embodiment of the present invention it is possible also to carry out transmission measurements with the use of two different deflector elements in the lid.

Here firstly the second deflector is not integrated in the side boundary of the receiving point but provided at another suitable point so that it is able to deflect the excitation light further horizontally into the sample.

For fluorescence measurement, the second deflector device can now suitably be mounted on a lid. In the same manner however it deflects the excitation light coming from below through the light-permeable side boundaries of the receiving point onto the sample to be analysed.

Secondly, in addition an alternative second light deflector for measuring transmission can be provided which is able to deflect the excitation light by multiple reflection into the receiving point and vertically downward through the sample. In other words excitation now takes place no longer horizontally but vertically, and also the radiation for transmission measurement is taken vertically from the sample. For such transmission measurements for example a roof prism, a truncated cone prism or another beam-deflecting component can be used in which the radiation is deflected by multiple deflection onto the sample to be analysed such that the radiation passes through the sample and can interact therewith, wherein the optical axis of the exciting radiation coincides with the optical axis of the radiation guided in the direction of the detector.

Suitably both said deflectors are integrated simultaneously in a lid which can be placed on the sample holder from above, so that for example by turning the lid through a constructionally defined angular dimension about its rotation axis, simple switching from transmission measurement to fluorescence measurement or vice versa is possible.

In this way it is thus possible to use fluorimeters and spectral fluorimeters not only for fluorescence measurement but also for transmission measurement.

It is thus possible, as already mentioned, to use for fluorescence measurement some photometers or spectrophotometers which are actually intended for absorption measurement or transmission measurement.

In a third embodiment the invention can also be used for measuring transmission in a transmission meter and fluorescence in a fluorescence meter, wherein the components are arranged so that the lid is turned for this. Here the second light deflector is able to deflect the excitation light coming from the first light deflector, through multiple reflection into the receiving point and vertically downward through the sample, wherein a side boundary of the sample holder, which delimits the latter in a direction at a right angle to said position, is designed as a chamfer of the sample holder totally internally reflecting the fluorescence light.

The advantage herein is that the respective measurement devices for transmission measurement or fluorescence measurement can be used without the slightest need to adapt any measurement routine or procedure. However the presence of both types of measuring device is essential.

When setting up a combination device for both transmission measurement and fluorescence measurement for example using individual modules, the two measurement modes can be operated simultaneously in the apparatus. This is possible with a modified arrangement of the components for beam deflection.

In a fourth embodiment of the present invention, a third light deflector is integrated next to the receiving point in the sample holder and arranged horizontally opposite the second light deflector, wherein said third light deflector is able to deflect downward the light coming from the second light deflector and passing through the sample to measure the transmission. Thus the apparatus according to the invention is equally suitable for measuring transmission in a transmission meter and fluorescence in a fluorescence meter, and by a different construction of the sample receiving point and integration of a second beam deflector in the light-permeable side boundaries of the sample receiving point, corresponding components arranged in the lid can be omitted.

The sample receiving point can here preferably be designed exchangeable in order to be able to use different optical layer thicknesses for transmission measurement.

BRIEF DESCRIPTION OF THE DRAWINGS

FIG. 1A shows a vertical section view of a first embodiment of the present invention;

FIG. 1B is a vertical section depiction rotated through 90° in relation to FIG. 1A; FIG. 1C is a horizontal section depiction along line A-A in FIG. 1A;

FIG. 2A shows an enlarged view of the actual measurement point in FIG. 1A; FIG. 2B corresponds to FIG. 2A in which however in addition some light beams are drawn to illustrate the light guidance;

FIG. 3A is a horizontal section depiction along line A-A of FIG. 1A with the beam arrangement of 90° typical for fluorimeters; FIG. 3B is an alternative section view corresponding to FIG. 3A for the beam arrangement of 180° typical for photometers for transmission measurement;

FIG. 4A shows an enlarged view of the actual measurement point in a second embodiment of the invention with rotatable lid, with the lid in a position for fluorescence measurement; FIG. 4B shows an enlarged view of the actual measurement point of the second embodiment with the lid in a position for transmission measurement;

FIGS. 5A and 5B are horizontal section views corresponding to FIGS. 3A and 3B, each with the beam arrangement of 90° typical for fluorimeters and the beam arrangement of 180° typical for photometers for transmission measurement;

FIG. 6A shows an enlarged view of the actual measurement point in a third embodiment of the invention for transmission measurement; FIG. 6B shows an enlarged view of the actual measurement point of the third embodiment for fluorescence measurement; FIG. 6C is a section view correspondingly along line A-A of FIG. 1A with a non-rotatable lid, wherein the apparatus must be inserted in another device in order to allow transmission measurements or fluorescence measurements;

WAYS OF IMPLEMENTING THE INVENTION

Figure 7A:
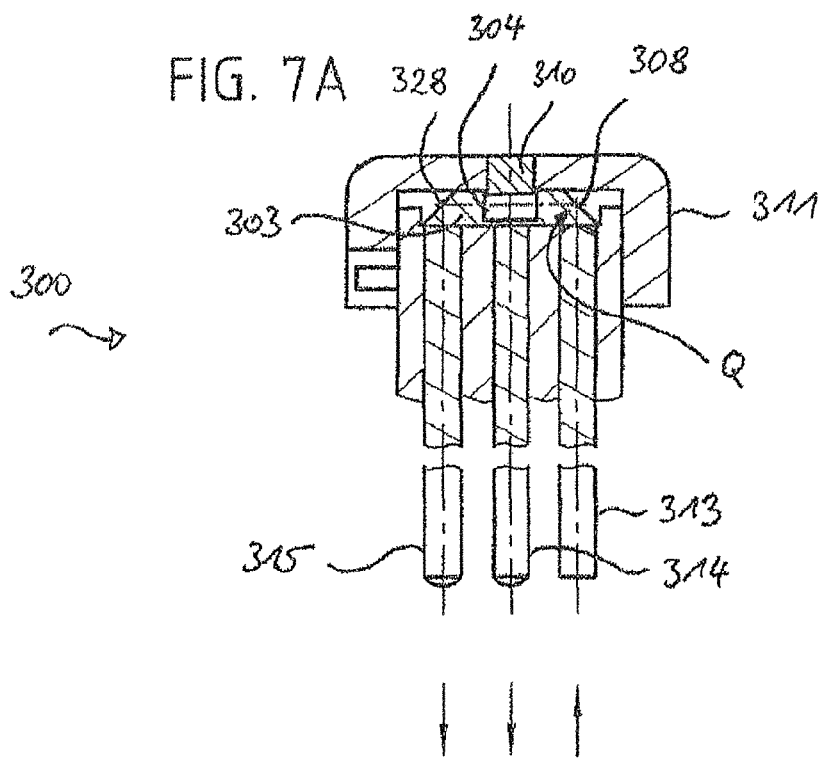
FIG. 7A shows an enlarged view of the actual measurement point in a fourth embodiment of the invention which is suitable for transmission measurement and fluorescence measurement.

FIG. 1A shows a vertical section view of the analysis apparatus according to the invention in a first embodiment of the invention, and FIG. 1B shows a vertical section view which is rotated by 90° about the drawn vertical axis in comparison with FIG. 1A. The analysis apparatus 1 comprises a vertical, oblong housing with square cross section (see FIG. 1C) which at its top has a sample holder 3 with a dish-like recess 4 to receive a small amount of a liquid sample P, such as for example a drop, wherein the order of magnitude of the sample volume applied lies in the region of 10 µl or less. In this view and in the corresponding views of the embodiments described below, the analysis apparatus 1 is shown already in its normal working position in which the liquid sample P is introduced into the sample receiving 4 from above and there held by gravity. The sample holder 3 consists of a material which is transparent to excitation light and the fluorescence signal generated thereby in the sample or other signal types such as Raman scattering, and in the present case is made of a suitable glass such as synthetic quartz glass. However not all boundary surfaces of the sample holder 3 need necessarily be transparent in this way, but merely those surfaces through which the excitation light and the signal to be measured pass.

The apparatus is closed at the top by a lid 11 in which a reflector 10 is inserted centrally above the sample receiving point 4 and which delimits the sample receiver 4 at the top. Although the apparatus shown in the present embodiment is delimited at the top by a reflector 10, it is also conceivable for the sample receiving point 4 to be delimited only by a lid 11 in order to define precisely the very small sample volumes. The reflector 10 of the present embodiment protrudes slightly into the receiving point in order to prevent the liquid sample from escaping when the lid 11 is closed. Similarly it is possible to design the reflector flush with the top of the sample holder 3, wherein the same applies to the alternative embodiment in which the sample receiving point 4 is delimited merely by the lid 11.

The analysis apparatus 1 is intended to be inserted in a receiving of a conventional spectral analysis device, wherein the analysis device can be a spectrophotometer, fluorimeter, Raman spectrometer or absorption meter or similar, which can measure the fluorescence, luminescence, phosphorescence, Raman scattering or absorption of the liquid sample P.

To this end the analysis apparatus 1 in its bottom region, i.e. below the sample holder in the working position, has a horizontally oriented light inlet 5 for excitation light which is located at a suitable position to couple in excitation light from said meters through the light inlet opening 5 when the analysis apparatus 1 is used. The analysis apparatus also comprises a suitably positioned light outlet 6 for coupling out the signal light at the meter.

As a first deflector device for the light, a reflecting prism 7 is provided in the beam path downstream of the light inlet 5 and couples in the excitation light beam from the horizontal into a light guide 13, for example a light-conducting fibre, provided vertically in the housing 2 of the apparatus 1. It is also possible to use other light deflector elements such as mirrors instead of reflecting prisms. The excitation light is thus guided through the deflector or reflector at the prism 7 and—in this embodiment—guided by the light conductor 13 upward to a position at the side of the receiving point 4. It is however also possible to omit the light guide and guide the excitation beam for example through a hollow housing interior to the position next to the receiving point 4.

Furthermore in the present embodiment, above the end of the light conductor at the position at the side of the receiving point 4, a chamfer 8 is formed in the side wall of the sample holder 3 as a second light deflector 8, which deflects the excitation light beam by total internal reflection into the horizontal with respect to the sample P in the sample receiver 4 (see FIG. 1A). The excitation light generates in the sample P for example fluorescence which is emitted substantially vertically (90°) to the direction of incidence of the excitation light in the sample P into a narrow spatial angle. In the present description fluorescence is used merely as an example for the generation of emission, since the structure of the analysis apparatus 1 creates no differences for analysis of other emission types such as luminescence, phosphorescence or Raman scattering which are also observed at an angle to the direction of the excitation light, in order to be able to separate the very weak signals from the high intensity of the excitation light. It must also be understood that for practical reasons, the observation or diversion of the emission light takes place presently at 90° to the excitation direction, but in principle it is also possible to use another angle which guarantees a sufficient spatial separation of the excitation light and signal light.

Part of said fluorescence light is radiated upward and reflected back down by the reflector 10. Together with the part emitted downward, the fluorescence light is coupled in through the base or bottom flat boundary of the sample holder 4 into a second light guide 14 which guides the fluorescence light to a reflection prism 9, also located in the bottom region of the apparatus, as a first detector-side light deflector, which in turn deflects the fluorescence light beam to the detector located in the fluorescence meter. For this a light outlet opening 6 is provided in the housing 2 of the analysis apparatus 1 and is also oriented horizontally and, corresponding to the beam guidance of the fluorescence meters, is arranged at an angle of 90° to the light inlet 5 as evident from FIGS. 1B and 1C.

FIGS. 2A and 2B show again in enlarged view the top region of the analysis apparatus 1, wherein in FIG. 2B as an example light beams are shown which are coupled into the sample holder 3 as excitation light through the light guide 13 at the side next to the sample receiver 4, totally internally reflected by the chamfer 8 as the second light deflector and guided horizontally into the sample P. The fluorescence radiation (emission) is then guided away by the light guide 14 down at a right angle out of the sample receiver 4 of the sample holder 3.

FIG. 3A again shows a section view corresponding to FIG. 1C along line A-A of FIG. 1A. However the invention provides as an alternative that the fluorescence emission is coupled out of the analysis apparatus 1, not at a right angle to the direction of the exciting radiation but aligned therewith. Here in the corresponding section view shown in FIG. 3B, the light outlet opening 6' is formed in the side of the analysis apparatus 1 opposite the light inlet opening 5. In this way it is possible to use a commercial photometer or spectrophotometer, which is actually designed for absorption measurement, also to measure fluorescence, since by the arrangement shown in FIG. 3B, the fluorescence radiation is coupled out of the analysis apparatus 1 aligned with the exciting radiation, and can be coupled into the photometer or spectrophotometer according to the aligned excitation and signal beam paths. Thus fluorescence measurements can be carried out irrespective of the device-side arrangement of excitation beam path and emission beam path.

FIGS. 4A and 4B show a second embodiment of the analysis apparatus according to the invention which can be used both to measure fluorescence and to measure the absorption properties of the liquid sample P in the sample receiving point 4. FIG. 4A shows a detailed view of the upper part of the analysis apparatus 100 in which the second light deflection is achieved by two optical deflector elements 108 and 118 which can be used alternatively. The one deflector element is designed as an externally reflecting prism 108, which is mounted on the side and below the lid 111 of the apparatus 100 such that with its base 108a it is arranged above the light guide 113 for the excitation light and deflects the excitation light beam by 90° in order to introduce it horizontally into the sample in the sample receiver 4. In contrast to the first embodiment, here the sample holder 103 does not extend right into the region above the light guide 113 for the excitation light, but the light emerges from the light guide 113 at the end of the housing 102 of the apparatus 100 before it is deflected into the horizontal by the reflector prism 108. Thus suitably the end of the light guide 113 is equipped with a lens or lens-like surface 123 to bundle the excitation light beam. In this way according to the same principle of the first embodiment, the sample liquid in the sample receiver 4 can be excited to fluorescence emission, wherein the fluorescence radiation emitted—as in the first embodiment—is guided by a light guide 114 vertically downward in order to be guided horizontally to a detector in the lower region of the apparatus 100 again by the first detector-side light deflector 9. Optionally also a lens or lens-like curved surface 124 can be formed at the lower end of the light guide 114.

Furthermore a roof prism 118 is mounted eccentrically below the lid 111 and terminates or delimits the sample receiver 4 with its broader underside. Suitably the roof prism 118, in its part 118a above the sample receiver 4, has on the underside a small projection which prevents the escape of the sample fluid from the dish-like recess 4. (For the sake of clarity, the protrusion is not shown extending up to the edges of the sample receiver). The left part 118b of the underside of the roof prism 118 visible in FIG. 4A does not come to lie on the sample receiver 4.

If now the lid 111 is rotated by 180° (see FIG. 4B which shows the same section view as FIG. 4A, not rotated by 90°), the part 118b of the underside of the roof prism 118 which was not previously above the sample receiver 4, comes to lie above the light guide 113 guiding the exciting radiation, so that the light beam emerging from the light guide 113, after passing through a short gap 119 located laterally next to the sample receiver 4, enters the roof prism 118 through surface 118b, is totally internally reflected into the horizontal by a chamfered side 118c of the prism 118, this reflected excitation light is then reflected vertically downward over the sample receiver 4 from the other chamfered side 118d of the roof prism 118, and thus enters the sample receiver 4 vertically and is transmitted through the sample P. The transmitted light, which enters the light guide 114 through the base of the sample receiver 4, now contains the absorption signature of the sample P and can therefore be analysed to determine the absorption properties of the sample P. It should be noted that the arrangements of the reflection prism 108 and the roof prism 118 shown in FIGS. 4A and 4B, and their integration in the lid 111, should be regarded merely as examples and that also other deflector elements such as for example a mirror can be provided at the positions of surfaces 108a, 118c and 118d. It is also possible to arrange these optical deflector elements at other angular arrangements so that the lid can be turned about the vertical axis through an angle other than 180° in order to switch from the configuration for fluorescence measurement to the configuration for absorption measurement.

As already shown in the first embodiment in FIGS. 3A and 3B, in the embodiment in FIGS. 4A and 4B too, the light outlet opening can be arranged at 90° to the light incident opening in the housing of the analysis apparatus 1 (FIG. 5A), wherein the apparatus 100 can then be inserted in conventional fluorescence meters. Alternatively the light outlet opening 6' can also be arranged at 180°, i.e. aligned with the light inlet opening on the opposite side of the housing of the apparatus 100, so that measurements of fluorescence/luminescence (FIG. 4A) and absorption (FIG. 4B) can be carried out in a photometer or spectrophotometer (FIG. 5B).

FIGS. 6A to 6C show a third embodiment of the present invention. It should be noted now that FIGS. 6A and 6B again—like FIGS. 1A and 1B—show section views rotated by 90°. In this embodiment the analysis apparatus 200—like the first and second embodiments—comprises a light guide 213 which guides the excitation light from the first light deflector 207 next to the sample receiver 4. Above the sample holder 203 and arranged eccentrically is a frustoconical prism 218 which, as a second light deflector like that in the second embodiment, deflects the excitation light so that it is conducted vertically into the sample receiver 4 and transmitted through the sample P. Accordingly a light guide 214 is again provided along the vertical axis of the apparatus 200 and (as in the operating mode in FIG. 4B of the second embodiment) guides the transmitted light carrying the absorption signature vertically downward. There it is deflected into the horizontal by a second detector-side light deflector 209' and coupled out of the analysis apparatus 200 via a light outlet opening 206' which is arranged aligned with the light inlet opening 205 on the opposite side of the housing.

At the same time, in this embodiment the sample holder 203 comprises a chamfer 228 on a side wall as a third light deflector at a position which is rotated by 90° from the position at which the excitation light coming from the first light deflector is guided by the light guide 213 next to the sample receiver 4 (see FIGS. 6B and 6C). This chamfer 228 is also located at the side next to the sample receiver 4 on the same horizontal level as this and serves to reflect vertically downward, by total internal reflection, into the sample holder 203 the fluorescence generated in the sample by the excitation light beam passing vertically through it, which is emitted into the horizontal substantially at 90° to the excitation light beam in the sample. This fluorescence light emerges from the sample holder 203 vertically through its lower boundary surface and into a third light guide 215 which guides the fluorescence emission downward to a second detector-side light deflector 209, which deflects the fluorescence emitted radiation into the horizontal and couples it out through a light outlet opening 206. This light outlet opening 206 is again arranged at 90° to the light inlet opening, as suitable for fluorescence measurements. The third light deflector—like the first and second detector-side light deflectors of this embodiment—can again be formed by deflector prisms, mirrors or other suitable light-deflecting elements.

Figure 7B:
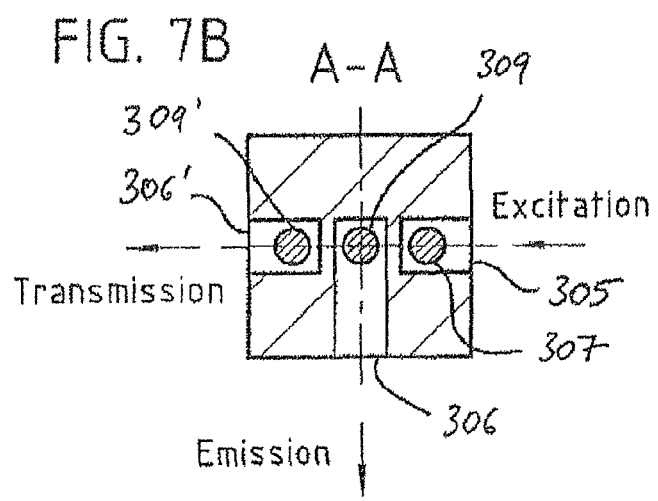
FIG. 7B is a corresponding section view along line A-A of FIG. 1A with a non-rotatable lid, wherein the apparatus must be inserted in another measuring device in order to allow transmission measurements or fluorescence measurements.

FIGS. 7A and 7B show a fourth embodiment of the present invention. This embodiment shows a variant of the third embodiment in which the sample holder 303 has two chamfers 308, 328 on opposite boundary sides. The chamfer 308 shown on the right in FIG. 7A—as in the first embodiment—serves for total internal reflection of the excitation light supplied by the light guide 313 and conducts this excitation light beam horizontally to the sample receiver 4 and through the sample P. The fluorescence/luminescence excited in the sample as a result is received by a light guide 314 at 90° and guided vertically down to a first detector-side light deflector 309. The excitation light beam passing horizontally through the sample is guided further into the sample holder to the second chamfer 328, which now also deflects vertically downward the transmitted light beam carrying the absorption signature, and couples it into a light guide 315. This guides the transmitted light to a second detector-side light deflector 309'. The first detector-side light deflector 309 deflects the light beam with the fluorescence signal horizontally through a light outlet opening 306 which is arranged at 90° to the direction of the excitation light beam and the light inlet opening 305. The second detector-side light deflector 309' however deflects the transmitted light beam (absorption spectrum) horizontally through a light outlet opening 306' arranged opposite the light inlet opening 305.

Thus the third and fourth embodiments of the analysis apparatus 200 or 300 can be used as required for analysis of the transmitted light (absorption) or emitted light (fluorescence, luminescence, Raman scattering etc.) in the corresponding measurement devices without the need to make changes to the analysis apparatus, for example rotation of the lid.

Figure 8A:
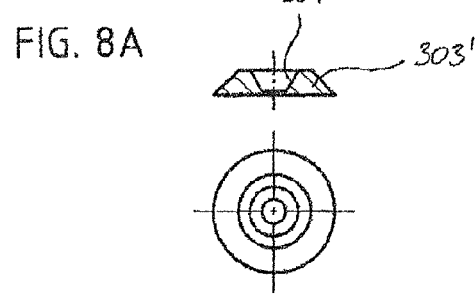
FIGS. 8A to 8D show variants of the sample holder and receiving points.
Figure 8B:
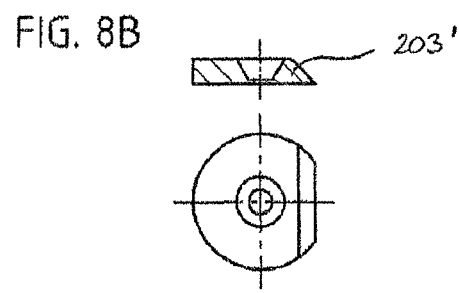
Figure 8C:
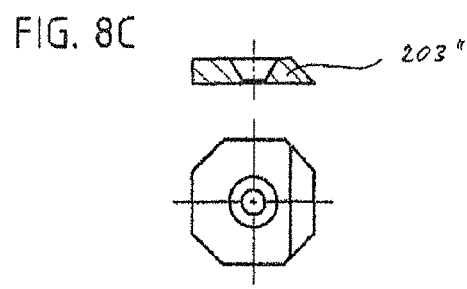
Figure 8D:
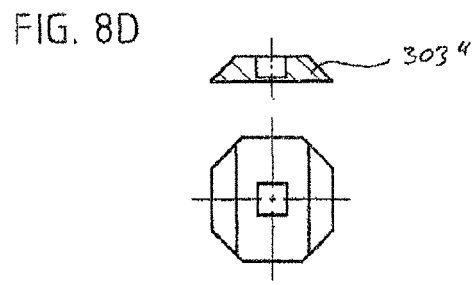

FIGS. 8A to 8D finally show constructional variants of the sample receiver according to the invention, wherein FIG. 8A shows an alternative sample receiver 303' suitable for the fourth embodiment with a dish-like sample receiving point 304' instead of a cylindrical one, in side view and top view; FIG. 8B shows a sample receiver 203' suitable for the third embodiment. Both variants have a round cross section. FIGS. 8C and 8D however show sample receivers 203" and 303" with octagonal cross section, wherein FIG. 8C again is suitable for the third embodiment and has a dish-like recess while the sample receiver in FIG. 8D is a sample receiver suitable for the fourth embodiment.

It should be understood that in the embodiments described above, the horizontal cross section along line A-A need not necessarily be formed square but can have other forms, for example octagonal or round, depending on the requirements of the receiver in the respective measurement devices. Thus the analysis apparatus preferably has the external dimensions of a cell which can be suitably inserted in a photometer, spectrophotometer, fluorimeter or spectral fluorimeter and exposed to this light. The external dimension of the cross section of the analysis apparatus thus corresponds for example to that of a standard cell, and is in particular 12.5 mm×12.5 mm, since the majority of photometers or similar measuring devices are formed for such dimensions. The devices for light guidance or light deflection arranged in the interior of the analysis apparatus are here suitably arranged at the point on the analysis apparatus at which, with conventional cells, inlet and outlet windows are provided for the light serving for measurement, wherein the first light deflector deflects the light irradiated by the photometer or similar to the sample receiving point and the detector-side deflector(s) deflects the light coming back from the sample receiving point to the detector. By suitable choice of dimensions of the analysis apparatus according to the invention, this can thus be used in conventional photometers, spectrophotometers, fluorimeters or spectral fluorimeters in order there to be able to serve for measurement of even very small samples of a medium.

It should also be understood that in the description above, in the detection of emitted radiation at 90° to the exciting radiation, not all signatures to be analysed are listed, but this is evident to the person skilled in the art. Thus for example Raman scattering is measured at 90° to the incident exciting radiation, as is fluorescence or luminescence.

The association of the exciting radiation and emitted radiation with components, as made in the drawings and explanations, as well as the orientation of the beams, is merely a preferred association which allows to exploit all advantages described. In principle the analysis apparatus can also be operated inversely.

COMMERCIAL APPLICABILITY

Fluorescence in minute volumes, as well as UV/Vis spectroscopy, is used amongst others in molecular biology since the high measurement sensitivity of the method significantly lowers the detection limit for nucleic acids and proteins (from the lower ng/μl to the lower pg/μl region).

In addition, by suitable selection of fluorescence dyes such as e.g. SYBR green, a distinction can be made between nucleic acids (dsDNA, ssDNA, RNA), which is not possible using UV measurement at 260 nm alone since all nucleic acids absorb at precisely this wavelength.

The combination of UV/Vis spectroscopy and fluorescence in one measurement head brings the user a substantial potential for saving due to the lower investment requirement and significantly reduced requirement for space in the laboratory. At the same time the user need only learn the operation of one apparatus since he can cover both methods optimally with one measurement device.

The invention claimed is:

1. An apparatus for analysing or measuring fluorescence, luminescence, phosphorescence, Raman scattering or absorption in a small amount of a liquid sample using light which can be guided through the sample and then detected or analysed according to said measurement methods, the apparatus comprising:
   a sample holder disposed at the top in a working position with a receiving point for application or dripping of the sample;
   a light inlet oriented horizontally in the working position below the sample holder for excitation light that forms a beam;
   a first light deflector located downstream of the light inlet in a beam path to deflect the beam upward to a position next to the receiving point;
   a second light deflector which deflects the light beam coming from below horizontally into the sample to be analysed to excite fluorescence; and
   an alternative second light deflector to measure transmission, the alternative second light deflector able to deflect the excitation light by multiple reflections downward into the receiving point and vertically through the sample.

2. The apparatus according to claim 1, wherein the receiving point is a recess in the sample holder and is closed at the top.

3. The apparatus according to claim 1, wherein the second light deflector and the alternative second light deflector are integrated in a lid which can be placed on top of the sample holder and is designed rotatably such that it allows switching between the second light deflector to measure fluorescence and the alternative second light deflector to measure transmission.

4. The apparatus according to claim 1, further comprising:
   a detector light deflector located in a beam path below the receiving point and is able to deflect to a detector signal light emitted from or transmitted through the sample, the detector light deflector configured to deflect the signal light in a horizontal direction in the working position.

5. The apparatus according to claim 4, further comprising: a light outlet provided in the beam path downstream of the detector light deflector, the light outlet arranged such that the signal light deflected along the horizontal direction is passed through the light outlet, the horizontal direction being at 90° to the incidence direction of the excitation light.

6. The apparatus according to claim 4, further comprising:
   a light outlet provided in the beam path downstream of the detector light deflector, the light outlet arranged such that the signal light deflected along the horizontal direction is passed through the light outlet, the horizontal direction being aligned with the incidence direction of the excitation light.

7. An apparatus for analysing or measuring fluorescence, luminescence, phosphorescence, Raman scattering or absorption in a small amount of a liquid sample using light which can be guided through the sample and then detected or analysed according to said measurement methods, the apparatus comprising:
   a sample holder at the top in a working position with a receiving point for application or dripping of the sample, and a light inlet oriented horizontally in the working position below the sample holder for excitation light that forms a light beam;
   a first light deflector located downstream of the light inlet in a beam path to deflect the light beam upward to a position next to the receiving point;
   a second light deflector which deflects the light beam coming from below into the sample to be analysed; and
   a third light deflector provided next to the sample receiving point which is able to deflect vertically downward signal light generated by the excitation light passing vertically through the sample, the signal light emitted horizontally from the sample,
   wherein the second light deflector is able to deflect the excitation beam coming from the first light deflector by multiple reflections into the receiving point and vertically downward through the sample.

8. The apparatus according to claim 7, wherein the second light deflector is integrated in the sample holder at position next to the receiving point and is able to deflect the excitation light for excitation of fluorescence horizontally into the sample.

9. The apparatus according to claim 8, wherein the second light deflector is integrated in a side boundary of the sample holder and is formed as a chamfer of the sample holder which totally internally reflects the excitation light coming from the first light deflector.

10. The apparatus according to claim 7,
wherein the third light deflector is integrated in a side boundary of the sample holder which delimits the sample holder in the horizontal direction at a right angle to said position.

11. The apparatus according to claim 7, further comprising:
a first detector light deflector which is arranged in a beam path below the receiving point and is able to deflect to a detector the transmitted light coming from the sample in a first horizontal direction in the working position; and
a second detector light deflector which is located in a beam path below the third light deflector and is able to deflect to a detector the signal light coming from the sample and deflected by the third light deflector, the second detector light deflector configured to deflect the signal light in a second horizontal direction in the working position.

12. The apparatus according to claim 11, further comprising:
a first light outlet provided in the beam path downstream of the first detector light deflector, said first light outlet arranged such that the transmitted light deflected along the first horizontal direction is passed through the first light outlet, the first horizontal direction being at 90° to the incidence direction of the excitation light; and
a second light outlet provided in the beam path downstream of the second detector light deflector, said second light outlet arranged such that the signal light deflected along the second horizontal direction is passed through the second light outlet, the second horizontal direction aligned with the incidence direction of the excitation light.

13. The apparatus according to claim 12, wherein the first light deflector firstly and the first or second detector light deflector secondly are arranged on the same horizontal level.

14. The apparatus according to claim 11, further comprising:
a first light outlet provided in the beam path downstream of the first detector light deflector, said first light outlet arranged such that the transmitted light deflected along the first horizontal direction is passed through the first light outlet, the first horizontal direction being aligned with the incidence direction of the excitation light; and
a second light outlet provided in the beam path downstream of the second detector light deflector, said second light outlet arranged such that the signal light deflected along the second horizontal direction is passed through the second light outlet, the second horizontal direction being at 90° to the incidence direction of the excitation light.

15. An apparatus for analysing or measuring fluorescence, luminescence, phosphorescence, Raman scattering or absorption in a small amount of a liquid sample using light which can be guided through the sample and then detected or analysed according to said measurement methods, the apparatus comprising:
a sample holder at the top in a working position with a receiving point for application or dripping of the sample, and a light inlet oriented horizontally in the working position below the sample holder for excitation light that forms a light beam;
a first light deflector located downstream of the light inlet in a beam path to deflect the light beam upward to a position next to the receiving point;
a second light deflector configured to deflect the light beam coming from below into the sample to be analysed;
a third light deflector provided next to the sample receiving point, the third light deflector configured to deflect vertically downward the light beam deflected by the second light deflector and transmitted along a horizontal direction through the sample; and
a vertical light guide arranged below the receiving point along a direction perpendicular to the horizontal direction and configured to guide fluorescence or luminescence light excited in the sample vertically downward,
wherein the third light deflector is integrated in a side boundary of the sample holder which is arranged horizontally opposite the second light deflector, and
wherein fluorescence or luminescence excited in the sample as a result is received by the light guide at 90° and guided vertically down to a first detector-side light deflector.

* * * * *